US00PP31112P3

(12) United States Plant Patent
Ukai

(10) Patent No.: US PP31,112 P3
(45) Date of Patent: Nov. 26, 2019

(54) ***LIGUSTRUM* PLANT NAMED 'GREEN GLOBAL'**

(50) Latin Name: *Ligustrum sinensis*
Varietal Denomination: Green Global

(71) Applicant: Kaneya Co., Ltd., Chita, Aichi (JP)

(72) Inventor: Takanori Ukai, Suzuka (JP)

(73) Assignee: Kaneya Co., Ltd., Chita, Aichi (JP)

( * ) Notice: Subject to any disclaimer, the term of this patent is extended or adjusted under 35 U.S.C. 154(b) by 0 days.

(21) Appl. No.: 15/932,996

(22) Filed: Jun. 7, 2018

(65) Prior Publication Data

US 2018/0359893 P1 Dec. 13, 2018

Related U.S. Application Data

(60) Provisional application No. 62/603,724, filed on Jun. 8, 2017.

(51) Int. Cl.
*A01H 5/00* (2018.01)
*A01H 6/00* (2018.01)
*A01H 5/12* (2018.01)

(52) U.S. Cl.
USPC ..... Plt./226
CPC ..... *A01H 6/00* (2018.05); *A01H 5/12* (2013.01)

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

A new and distinct variety of *Ligustrum* plant having a small leaf size and dwarf growth habit.

6 Drawing Sheets

Botanical classification: *Ligustrum sinensis.*
Varietal denomination: 'Green Global'.

BACKGROUND OF THE INVENTION

The present invention comprises a new and distinct variety of *Ligustrum* plant, botanically known as *Ligustrum sinensis*, referred to by the varietal name 'Green Global'. The new variety was discovered in 2006 in Suzuka, Japan as a result of a naturally occurring whole plant mutation of an unnamed and unpatented *Ligustrum sinensis* variety. The new variety was first asexually reproduced by cuttings in Suzuka, Japan in January of 2008. 'Green Global' is similar to its parental varietal in leaf color, but differs in leaf size, density, and internode length. When compared to *Ligustrum sinensis* variety named 'Swift Creek' (unpatented), 'Green Global' exhibits smaller leaves and lacks leaf variegation. Further, 'Green Global's small leaf size and dwarf growth habit help to distinguish 'Green Global' when generally compared to other *Ligustrum* varieties known to the breeder. 'Green Global' has been trial and field tested and has been found to retain its distinctive characteristics and remain true to type through successive propagations.

DESCRIPTION OF THE DRAWINGS

Except where otherwise indicated, the accompanying photographic drawings illustrate the new variety at 2 years of age, with the color being as nearly true as is possible with color illustrations of this type.

DESCRIPTION OF THE PLANT

Figure 1:
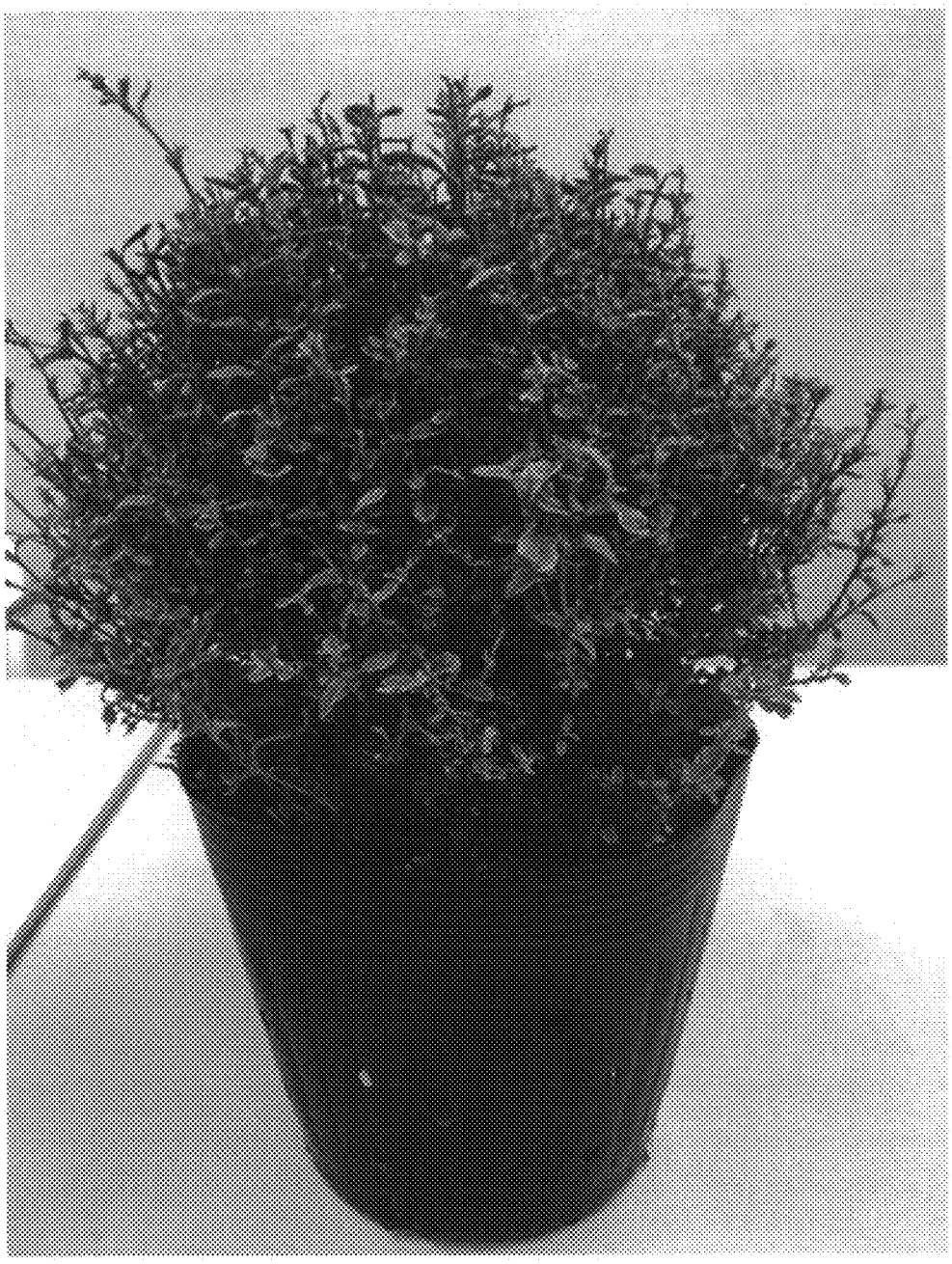
FIG. 1 shows an entire plant of the new variety.
Figure 2:
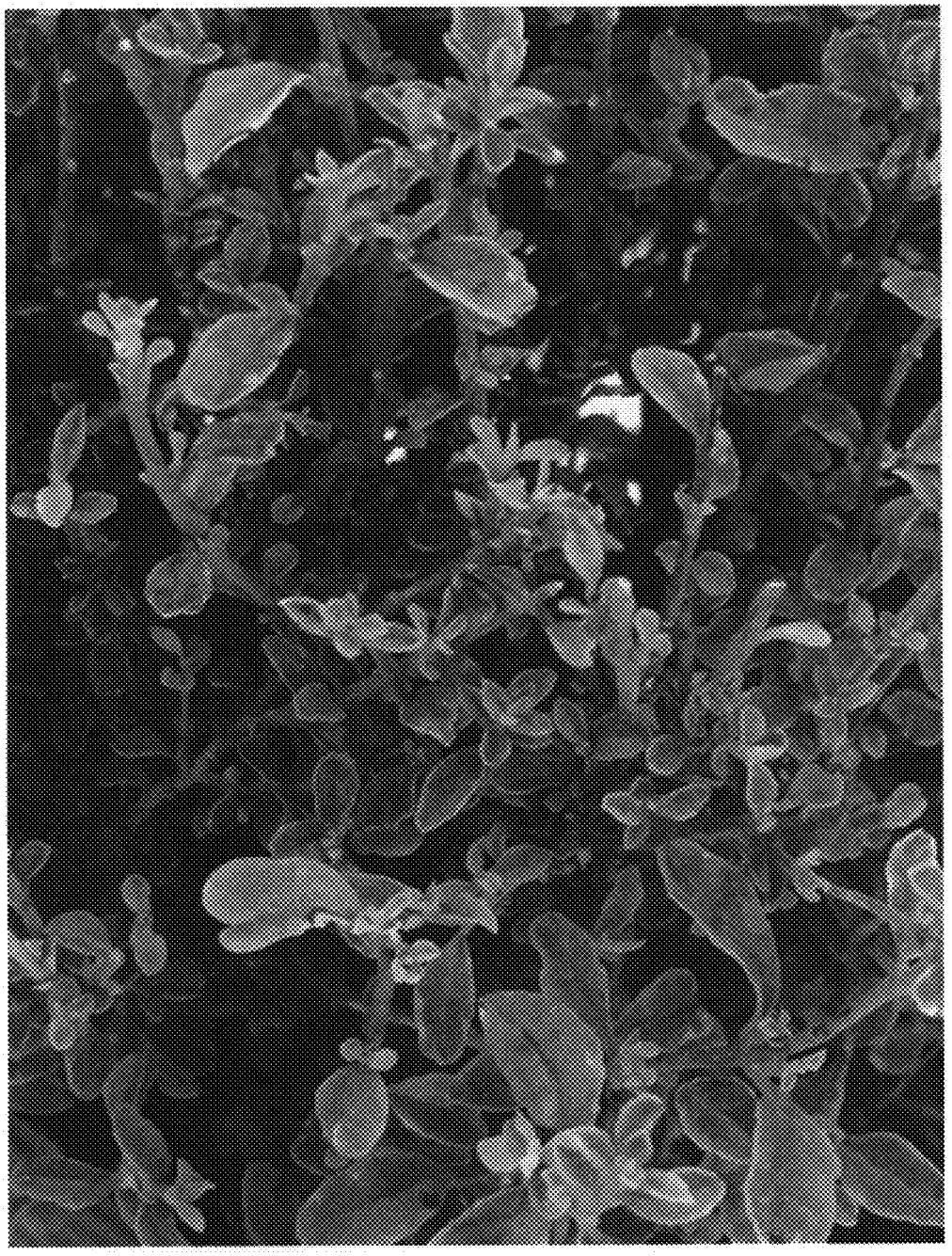
FIG. 2 shows a close-up view of branches and leaves of the new variety.
Figure 3:
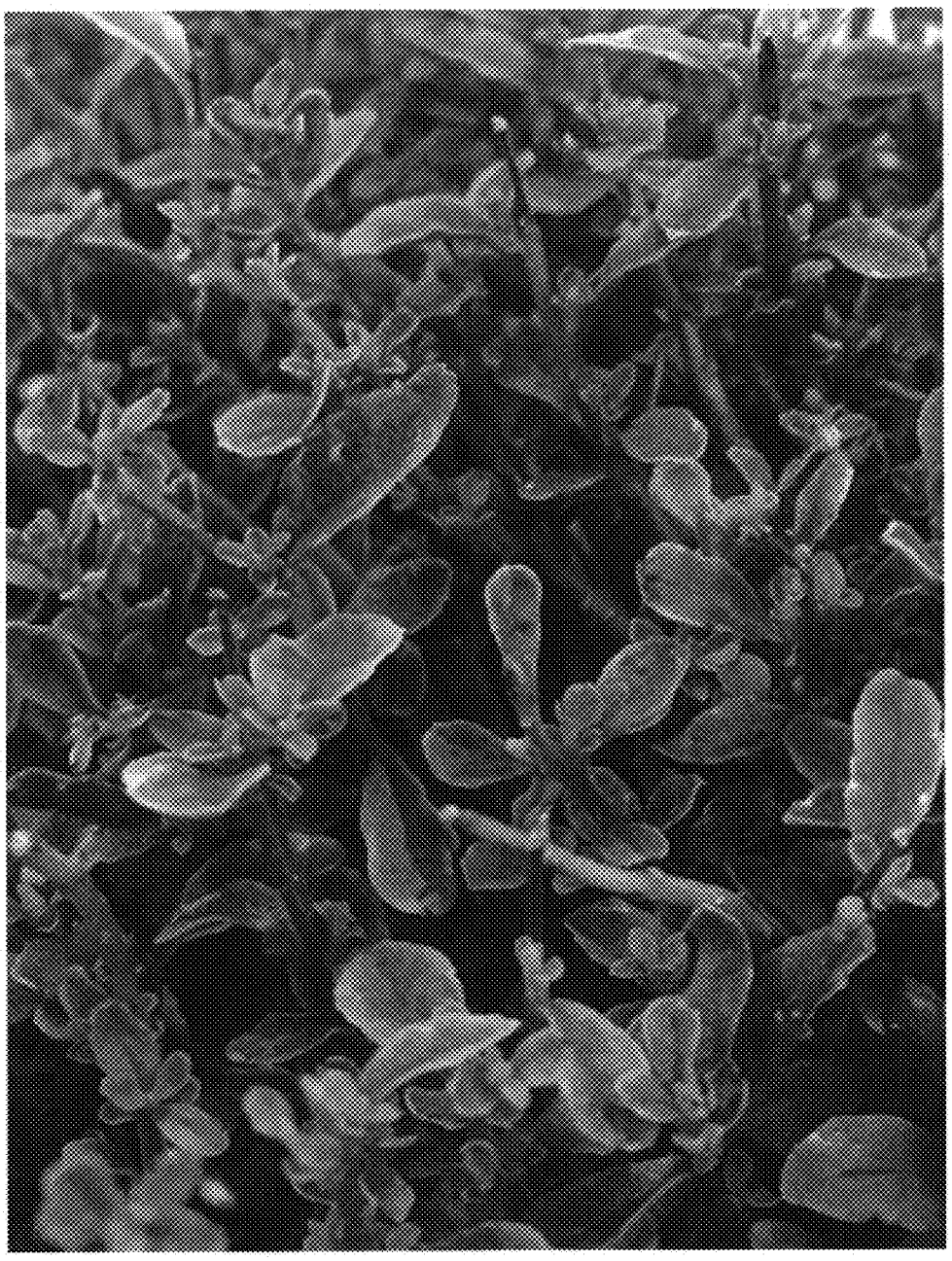
FIG. 3 shows a close-up view of branches and leaves of the new variety.
Figure 4:
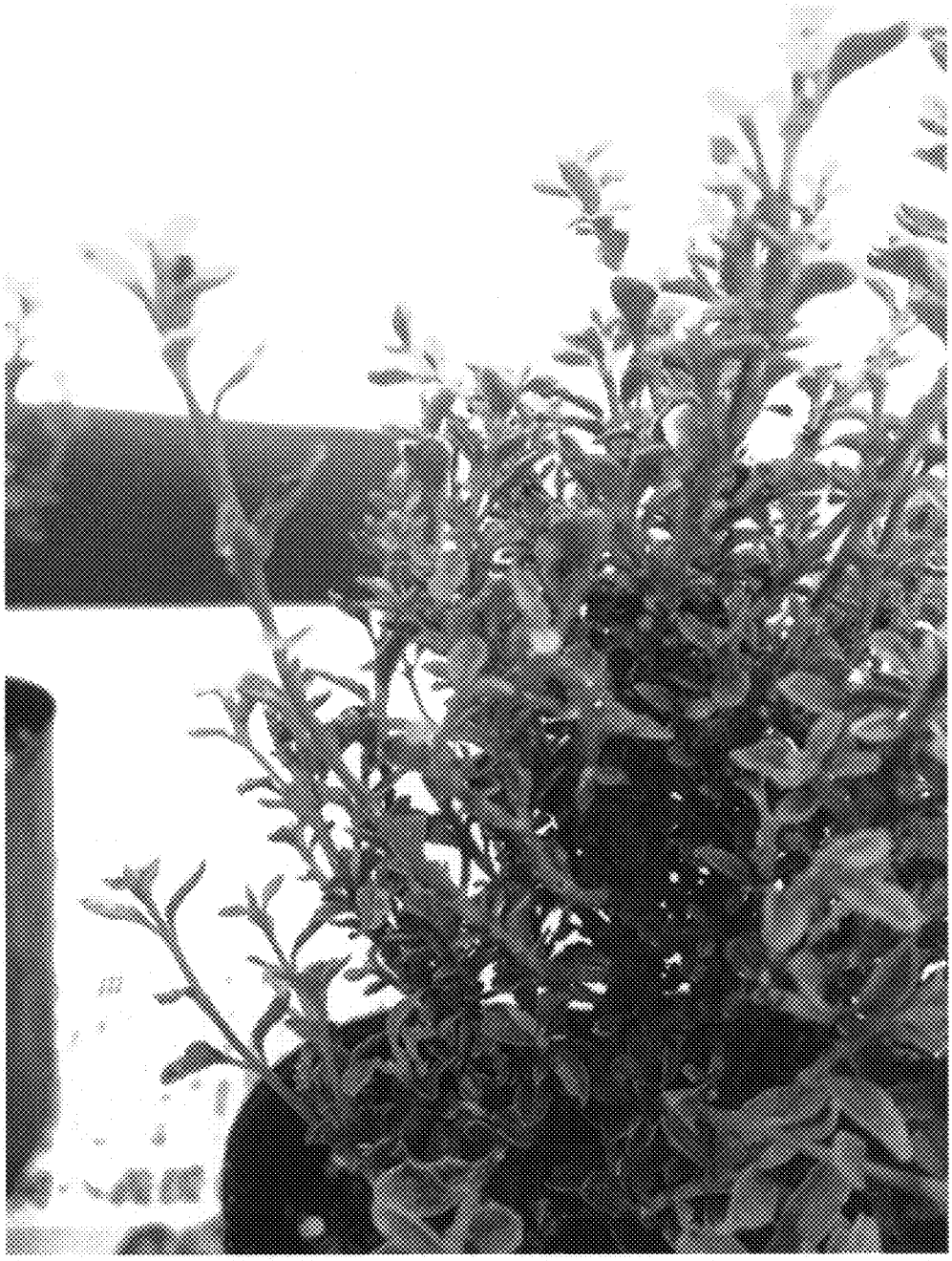
FIG. 4 shows a close-up view of lateral branches of the new variety.
Figure 5:
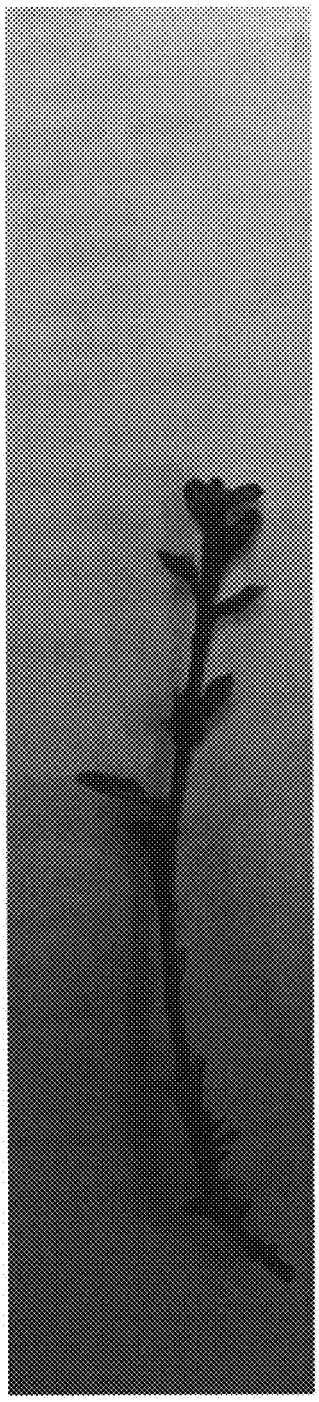
FIG. 5 shows a close-up view of a lateral branch of the new variety.
Figure 6:
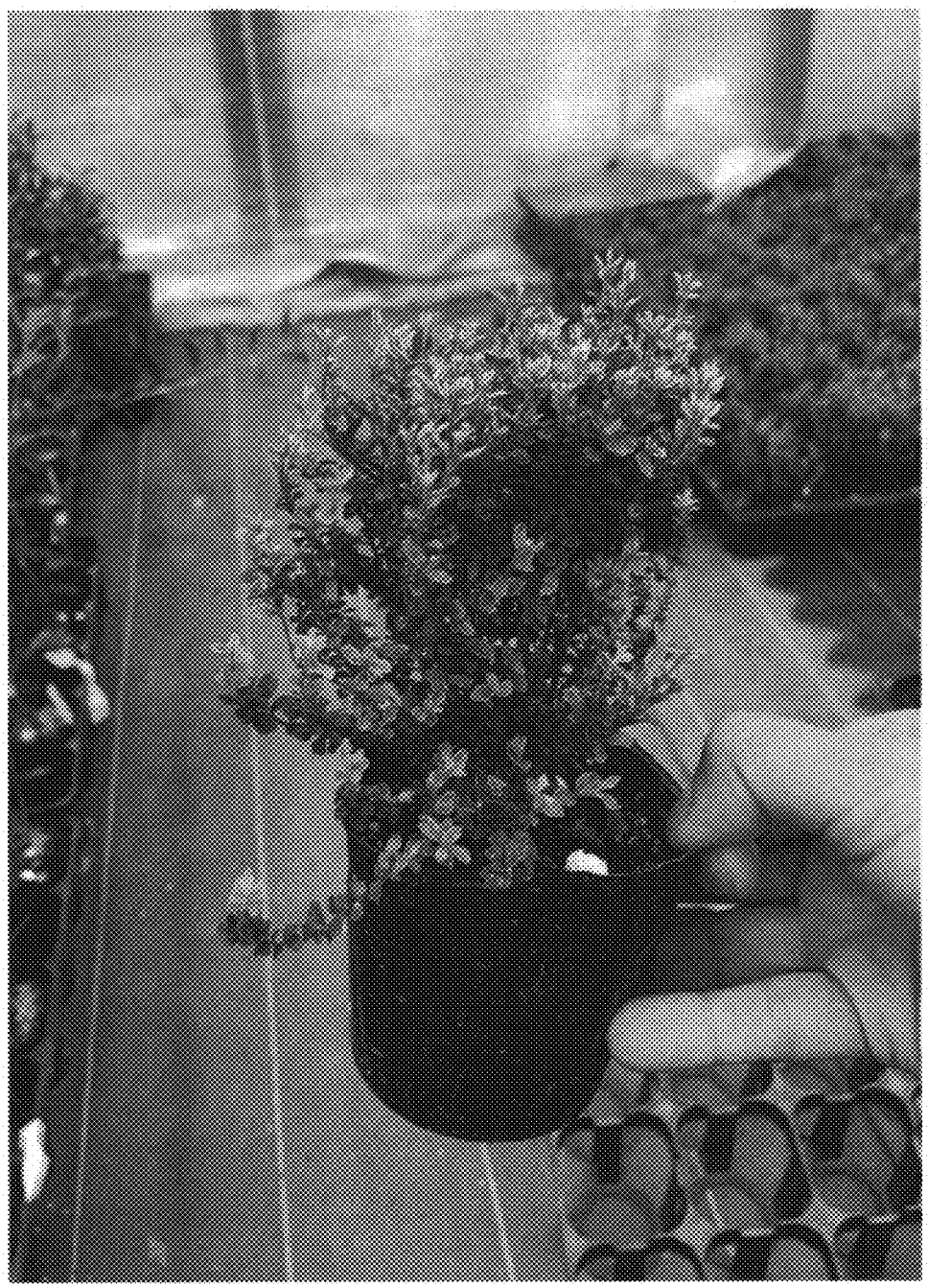
FIG. 6 shows an entire plant of the new variety at approximately 3 years from the sticking of a cutting from the mother plant.

The following detailed description sets forth the characteristics of the new variety. Plants of the new variety were grown outdoors in 15 cm pots, and the color readings and measurements were taken under artificial light on 2 year old plants in Mie Prefecture, Japan. Color references are primarily to The 2015 R.H.S. Colour Chart of The Royal Horticultural Society of London, Sixth Edition.

PLANT

Time to initiate roots: About 1 month in the winter under greenhouse conditions.

Time to produce a rooted plant: 3-5 months, depending on the season.

Root description: Exhibits dense roots with a fine to medium texture.

General appearance and form: Symmetrical, with a dwarf growth habit.

Height (from soil to top of branches): From 15 to 20 cm, with an average of 17.5 cm.

Plant diameter: From 15 to 30 cm, with an average of 20 cm.

Vigor: Slow.

Branching habit: Numerous.

Stems:

*Immature stem texture*.—Glabrous.

*Immature stem color*.—Green Group RHS 137C.

*Mature stem texture*.—Glabrous.

*Mature stem color*.—Yellow-Green Group RHS 148A.

Lateral branches:

*Appearance*.—Slender, with alternate leaves.

*Color*.—Yellow-Green Group RHS 148A.

*Texture*.—Glabrous.

*Length*.—From 2.5 to 7.5 cm, with an average of 5.5 cm.

*Diameter*.—From 1.3 to 2 cm.

*Internode length*.—From 0.3 cm to 5 cm, with an average of 0.4 cm.

*Strength*.—Strong.

*Quantity*.—Numerous.

Foliage:

*Persistence*.—Deciduous.

*Arrangement*.—Alternate.

*Number of leaves per branch*.—From 50 to 70, with an average of 60.

*Size of leaf*.—Length: From 0.5 to 1.5 cm, with an average of 1 cm. Width: From 0.3 to 0.5 cm, with an average of 0.4 cm.

*Shape of leaf* (*generally*).—Elliptical to ovate.

*Shape of apex*.—Acute.

*Shape of base*.—Cuneate.

*Texture* (*upper and lower surfaces*).—Glabrous.

*Margin type*.—Entire.

*Fragrance*.—None.

*Color*.—Young leaves: Upper surface: Green Group RHS 139B. Lower surface: Green Group RHS 137C. Mature leaves: Upper surface: Green Group RHS NN137A (Green Group RHS 136B in the fall). Lower surface: Green Group RHS 137C (Yellow-Green Group RHS 150D in the fall).

*Petiole*.—Length: From 0.1 to 0.4 cm, with an average of 0.3 cm. Diameter: From 0.05 to 0.2 cm, with an average of 0.1 cm. Color (upper and lower surfaces): Yellow-Green Group RHS 146A (Red-Purple Group RHS 61A in the fall). Texture (upper and lower surfaces): Glabrous.

*Veins*.—Venation pattern: Pinnate. Color: Upper surface: Green Group RHS NN137A. Lower surface: Green Group RHS 137C.

Disease/pest resistance: Nothing unusual noted to date.

Temperature tolerance: From −5 to +35° C.

Drought tolerance: Nothing unusual noted to date.

Flowers: None observed to date.

Seeds: None observed to date.

I claim:

1. A new and distinct variety of *Ligustrum* plant named 'Green Global', as is herein illustrated and described.

* * * * *